United States Patent [19]

Heller et al.

[11] Patent Number: 4,996,143

[45] Date of Patent: Feb. 26, 1991

[54] FLUORESCENT STOKES SHIFT PROBES FOR POLYNUCLEOTIDE HYBRIDIZATION

[75] Inventors: Michael J. Heller, Poway; Edward J. Jablonski, San Diego, both of Calif.

[73] Assignee: Syngene, Inc., San Diego, Calif.

[21] Appl. No.: 511,834

[22] Filed: Apr. 13, 1990

Related U.S. Application Data

[63] Continuation of Ser. No. 315,218, Feb. 23, 1989, abandoned, which is a continuation of Ser. No. 812,111, Dec. 23, 1985, abandoned.

[51] Int. Cl.$^5$ .............................................. C12Q 1/68
[52] U.S. Cl. ...................................... 435/6; 436/501; 436/800; 536/27; 935/78
[58] Field of Search .................... 435/6, 803; 436/501, 436/800; 537/27; 935/78

[56] References Cited

U.S. PATENT DOCUMENTS 4,542,104 9/1985 Stryer et al. ........................ 436/546
4,584,277 4/1986 Ullman ................................ 436/501
4,666,862 5/1987 Chan ................................... 436/501

FOREIGN PATENT DOCUMENTS 0070685 1/1983 European Pat. Off. .
84/03285 8/1984 World Int. Prop. O. .

Primary Examiner—Amelia Burgess Yarbrough
Attorney, Agent, or Firm—Pretty, Schroeder, Brueggemann & Clark

[57] ABSTRACT

Fluorescent stokes shift probes for polynucleotide hybridization assays are designed to provide predetermined nucleotide base unit spacings between the donor and acceptor fluorophores. When the probes are hybridized to the target polynucleotide the fluorophores paired for non-radiative energy transfer are separated by 2 to 7 nucleotide base units. The fluorophores are attached to the DNA or RNA probes by linker arms having lengths of 4 to 30 Angstroms. Fluorescein is a preferred donor for use with a Texas Red acceptor.

29 Claims, 2 Drawing Sheets 10-100 NUCLEOTIDE BASES
SINGLE PROBE WITH FIVE BASE
(n=5) SPACING OF FLUOROPHORES DUAL PROBES HYBRIDIZED
TO TARGET POLYNUCLEOTIDE SEQUENCES
WITH SIX BASE (n=6) SPACING

FLUORESCENT STOKES SHIFT PROBES FOR POLYNUCLEOTIDE HYBRIDIZATION This application is a continuation of application Ser. No. 07/315,218, filed Feb. 23, 1989, which is a continuation of application Ser. No. 812,111, filed Dec. 23, 1985.

FIELD OF INVENTION

The field of this invention is fluorescent labelled polynucleotide probes for use in polynucleotide (DNA or RNA) hybridization assays. In general, this invention is concerned with improving the properties of fluorescent labelled probes for more sensitive detection in hybridization assay systems. In particular it is concerned with the selection and unique positioning of two or more fluorophores which through an efficient energy transfer mechanism produce a fluorescent probe or probes with significantly improved detection properties.

BACKGROUND OF INVENTION

Hybridization assays may be employed for the detection and identification of DNA or RNA sequences. Published methods as used particularly in recombinant DNA research are described in *Methods of Enzymology*, Vol. 68, pp. 379–469 (1979); and Vol. 65, Part 1, pp. 468–478 (1968). One such method involving a preliminary separation of the nucleic acid fragments by electrophoresis is known as the "Southern Blot Filter Hybridization Method." See Southern E., *J. Mol. Biol.* 98, p. 503 (1975). A recent and more complete review of nucleic acid hybridization methods and procedures can be found in Meinkoth, J. and Wahl, G., *Analytical Biochemistry*, 138, pp. 267-284 (1984).

Fluorescent labeled synthetic polynucleotide probes are commercially available in the United States. Chemical methods for incorporating modified nucleotides into synthetic polynucleotides are described in the published PCT Application WO 84/03285, dated Aug. 30, 1985. The synthetic polynucleotide containing the modified nucleotide (usually referred to as a "linker arm nucleotide") can subsequently be derivatized with a fluorescent moiety. As described in the cited PCT application, only a single fluorescent moiety is attached to the probe.

Certain problems are encountered when using polynucleotide probes labelled with commonly available fluorophores such as fluorescein, rhodamine, pyrenes, etc. The most serious problem involves limited sensitivity for direct detection of the probe in the assay system. For most hybridization assays a sensitivity or detection level of at least $10^{-18}$ mole of labelled probe ($10^6$ target molecules) is required. While many fluorophores inherently have this level of sensitivity, secondary interferences from the sample and components in the assay system prevent these levels of detection from being reached. At a level of $10^{-18}$ mole of fluorescent probe, fluorescence from the sample itself, Rayleigh scatter, reflection from support materials (nitrocellulose filters, etc.) and in particular Raman (water) scatter can produce background signals many orders of magnitude higher than the signal from the fluorescent probe.

Ideally, improvement in detecting fluorescent probes in such assay systems could be obtained by selecting a fluorophore which has: (1) a large Stokes shift, that is, a large separation between the wavelengths for maximum excitation (EX) and the wavelength for maximum emission (EM); (2) a high quantum yield ($QY \geq 0.5$); (3) a high extinction coefficient ($EC \geq 30,000$); (4) an emission beyond 600 nm (red fluorescence); and (5) an excitation maximum close to a laser line (442 nm Helium-Cadmium or 448 nm Argon). Unfortunately, there are no common fluorophores which fully satisfy these criteria. For example, fluorescein (EX: 495 nm, EM: 525 nm, $QY = 0.5$) is a highly fluorescent label with an excitation maximum near a laser line, but has a Stokes shift of only ~30 nm.

It is known that a larger Stokes shift can be obtained by employing a pair of donor/acceptor fluorophores which have overlapping spectra and which are arranged in close proximity for non-radiative energy transfer between the donor and acceptor fluorophores. This form of energy transfer was proposed by Förster, who developed equations of transfer efficiency in relation to separation distances between the fluorophores. See, for example, Förster, Th., *Ann. Phys.* (Leipzig) 2:55-75 (1948). A recent summary of Förster's non-radiative energy transfer is given in "Principles of Fluorescent Spectroscopy," J. R. Lakowicz, Chapt. 10 (1983). The Förster mathematical analysis predicates that the closer the spacing of the fluorescent moieties the greater the efficiency of energy transfer. Prior experimental evidence confirmed this prediction.

Stryer and Haugland (Proc. Natl. Acad. Sci. 58, 719-729, 1967) reported experiments with variable spacing for an energy donor and acceptor pair attached to oligopeptides. An energy donor group and an energy acceptor group were attached to the ends of proline oligomers which served as spacers of defined lengths. Spacings of 1 to 12 units were tested, with a separation range of 12 to 46 Angstroms (Å). The longer oligomers were found to be in helical conformation. The energy transfer efficiency decreased from 100% at a distance of 12Å to 16% at 46Å. It was concluded that the dependence of the transfer efficiency on distance was in excellent agreement with the dependence predicted by the Förster equations. The results were so close to theoretical predictions that the authors proposed use of non-radiative energy transfer as a spectrocopic ruler. Related experiments with model systems reported by other researchers are confirmatory. See, for example, Gabor, *Biopolymers* 6:809-816 (1968); and Katchalski-Katzir, et al., *Ann. N. Y. Acad. Sci.* 366: 44-61 (1981). The use of the Förster energy transfer effect has been described in the following immunofluorescent assay patents. (See U.S. Pat. Nos. 3,996,345; 3,998,943; 4,160,016; 4,174,384; and 4,199,599). The energy transfer immunofluorescent assays described in these patents are based on the decrease or quenching of the donor fluorescence rather than fluorescent re-emission by the acceptor [Ullman, E. F., et al., *J. Biol. Chem.*, Vol. 251, 14, pp. 4172-4178 (1976)].

Homogeneous immunoassay procedures based on chemiluminescent labels or bioluminescent proteins have been reported which involve non-radiative energy transfer, see Patel, et al., *Clin. Chem.* 29 (9):1604-1608 (1983); and European Patent Application No. 0 137 515, published Apr. 17, 1985. By close spacing of the donor-acceptor group according to the principles of nonradiative energy transfer for high transfer efficiency it was proposed that homogeneous assays could be made practical. Homogeneous assays are inherently simpler to carry out but their use had been subject to the limitation that unbound labelled probe remains in solution and causes interfering background signal. European Patent Application No. 0 137 515 published Apr. 17, 1985 refers to various ligand-ligand interactions which can be used with the bioluminescent proteins including nucleic acidnucleic acid interactions. The examples, however, are directed to protein ligands rather than nucleic acids.

European Patent Application No.,0 070 685, published Jan. 26, 1983, relates to homogeneous nucleic acid hybridization assays employing non-radioative energy transfer between absorber/emitter moieties positioned within 100 Angstroms of each other. As described, the hybridization probes are prepared by attaching the absorber-emitter moieties to the 3' and 5' end units of pairs of single-stranded polynucleotide fragments derived from DNA or RNA by restriction enzyme fragmentation. The pairs of polynucleotide fragments are selected to hybridize to adjacent complementary sequences of the target polynucleotide with the labelled ends with no overlap and with few or no base-pairing spaces left between them. The preferred donor moiety is a chemiluminescent catalyst and the absorber moiety is a fluorophore or phosphore.

THE DRAWINGS

FIGS. 1 to 5 illustrate preferred embodiments of Stokes shift probes for use in practicing the invention.

SUMMARY OF INVENTION

This invention is based in part on the discovery that polynucleotides (DNA or RNA) provide an environment which strongly influences non-radiative energy transfer between donor-acceptor fluorescent moieties attached to polynucleotide probes. Prior to the present invention, it was not known how to design fluorophore-labelled probes with donor-acceptor moieties for practical and effective use with polynucleotides, particularly with regard to efficient emission by the acceptor fluorophore. It has been found that a novel spacing of the fluorescent moieties is critical for maximizing energy transfer and producing highly efficient fluorescent emission by the acceptor. Surprisingly, the optimum spacing requires intervening base pair units between the nucleotides to which the fluorescent moieties are attached. In particular, contrary to prior knowledge about Förster nonradiative energy transfer attachment of the fluorescent moieties to immediately adjacent nucleotide units (donor/acceptor distance 10–15Å) or with only a single intervening unit results in an unacceptably low transfer efficiency. The theoretical explanation for this new phenomenon is not known. However, it apparently relates to the formation of excitation traps when the fluorescent probe(s) is hybridized to the target polynucleotide. This "microenvironment" of the helical double-stranded polynucleotides has a marked effect on the optimum spacing for non-radiative energy transfer and efficient fluorescent emission by the acceptor.

More specifically, it has been found that for efficient acceptor emission the donor-acceptor fluorescent moieties should be separated when hybridized by at least two intervening base units but not over seven units. For optimum efficiency with either single probe or dual probe embodiments a separation range of from 3 to 6 base units is preferred. To maximize the benefits of this invention, the linker arm side chains which connect the fluorescent moieties to the nucleic acid (pyrimidine or purine) base units should have lengths within the range from 4 to 30 Angströms (Å) and preferably from about 10 to 25Å. With either the single or the double probe embodiments, neither of the fluorescent moieties should be attached to end units of the probes.

The probes of this invention are believed unique for the following reasons: (1) Unexpectedly, those donor and acceptor positions (e.g., distances of 20Å or less) predicted by the Förster equations and confirmed experimentally in model systems by prior investigators to provide maximum energy transfer efficiency were found to have minimal observed efficiency for hybridized polynucleotide probes. (2) Maximum observed energy transfer efficiency, "in terms of fluorescent emission by the acceptors" was found only for a relatively restricted number of positions requiring more nucleotide spacing between the fluorophores. (3) Maximum observed acceptor fluorophore emission was also found to be dependent upon hybridization of the probe to its complementary target sequence, viz., in the single probe embodiment efficiency was increased by hybridization. (4) With proper spacing an exceptionally high value (viz. 80%) for fluorescent emission by the acceptor fluorophore can be obtained.

DESCRIPTION OF PREFERRED EMBODIMENTS

Figure 1:
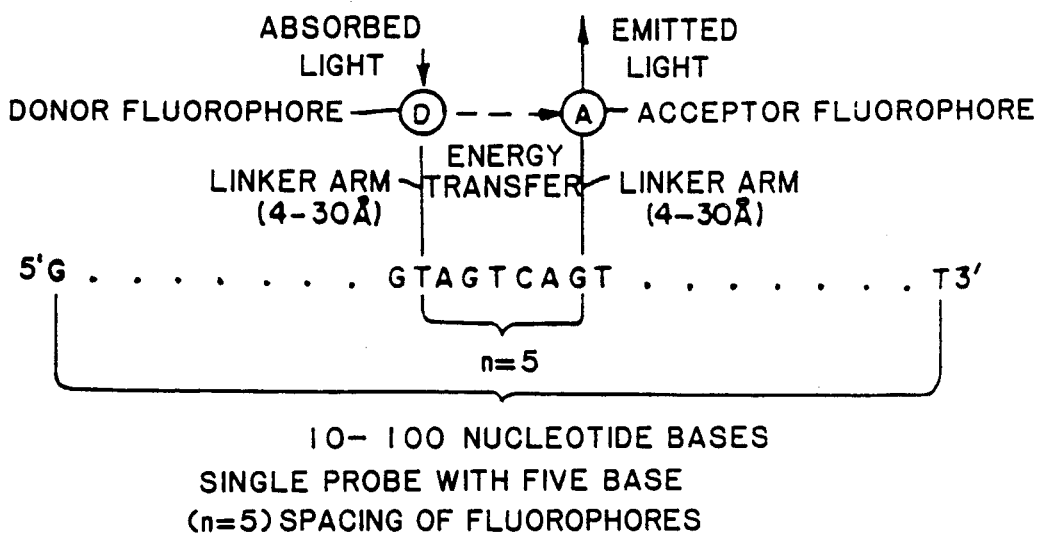

This invention is applicable to synthetic polynucleotide probes containing from 10 to 100 base units, and in particular 15 to 35 base units. With synthetically-prepared probes, precise attachment of the fluorophores can be obtained by the methods described in PCT Application WO 84/03285, published Aug. 30, 1984. This greatly simplifies the practice of the present invention with respect to preparation of the required probes.

Preferred embodiments of this invention utilize selected donor and acceptor fluorophore pairs appropriately positioned in single or dual polynucleotides. Such probes may be designed to produce a large Stokes shift and highly efficient acceptor fluorescent emission at wavelengths greater than 600 nm. In both the single and dual probe embodiments the fluorophores are attached to the polynucleotide with intervening base units as hybridized. The invention is generally applicable to plural probes, including triple and quadruple probes as well as dual probes.

One preferred embodiment utilizes fluorophores positioned near the end base units of dual polynucleotide probes. By avoiding attachment of either fluorophore to the terminal base units appropriate intervening base units are provided. Hybridization of the dual fluorophore probes to complementary target sequences can accurately position the donor and acceptor fluorophores according to the spacing requirements of this invention.

In the single probe embodiment, the donor and acceptor fluorophores should be attached to the polynucleotide probe at positions which give them a relative separation of two to seven intervening base units. In the dual probe embodiment, after both probes are hybridized to the target sequence, the donor fluorophore on one probe and the acceptor fluorophore on the other probe should also be attached to give a relative separation of two to seven base units. The preferred separation for both the single and dual probe embodiments is from 3 to 6 intervening base units. The optimized spacing is believed to be 4 to 5 units. In both single and dual probe embodiments when the probes are hybridized to the target polynucleotide the base units to which the donor and acceptor moieties are connected should be paired with base units of the target sample which are separated by 2 to 7 intervening base units.

Selection of Fluorophores

Selection of the donor and acceptor fluorophores is of importance to obtain the advantages of this invention. In general, the fluorescent moiety should comprise respectively donor and acceptor moieties selected so that the emission spectrum of the donor moiety overlaps the excitation spectrum of the acceptor moiety to produce efficient non-radiative energy transfer therebetween. Wavelength maximum of the emission spectrum of the acceptor moiety should be at least 100 nm greater than the wavelength maximum of the excitation spectrum of the donor moiety.

In addition, the fluorescent donor and acceptor pairs are preferably chosen for (1) high efficiency Forster energy transfer; (2) a large final Stokes shift (>100 nm); (3) shift of the emission as far as possible into the red portion of the visible spectrum (>600 nm); and (4) shift of the emission to a higher wavelength than the Raman water fluorescent emission produced by excitation at the donor excitation wavelength. For example, a donor fluorophore may be chosen which has its excitation maximum near a laser line (in particular Helium-Cadmium 442 nm or Argon 488 nm), a high extinction coefficient, a high quantum yield, and a good overlap of its fluorescent emission with the excitation spectrum of the acceptor fluorophore. In general, an acceptor fluorophore is preferably chosen which has a high extinction coefficient, a high quantum yield, a good overlap of its excitation with the emission of the donor, and emission in the red part of the visible spectrum (>600 nm).

Fluorescein is a particularly desirable donor moiety. Lucifer Yellow can also be employed as a donor moiety, particularly in combination with Texas Red as an acceptor moiety. The emission spectra of fluorescein (EX~492 nm, EM~520 nm, EC~70,000, QY high) and of Lucifer Yellow (EX~428 nm, EM~540 nm, EC~12,000, QY medium) both sufficiently overlap the excitation spectrum of Texas Red (EX~590 nm, EM~615 nm, EC~70,000, QY high). Fluorescein's excitation maximum (~492 nm) comes very close to the 488 nm Argon laser line and Lucifer Yellow's excitation maximum (~428 nm) comes very close to the 442 nm Helium-Cadmium laser line. In addition the fluorescein/Texas Red and Lucifer Yellow/Texas Red combinations provide large Stokes shifts of ~130 nm and ~170 nm respectively. In both cases the 615 nm to 620 nm Texas Red emission is at significantly higher wavelengths than the Raman water lines (~585 nm for 448 nm excitation and ~520 nm for 442 nm excitation). As compared with the use of a fluorescein reporter group alone, the combination with a Texas Red acceptor provides a ten to twenty fold increase in the relative detection sensitivity in the 615 nm to 620 nm emission region for excitation at ~490 nm. As compared with the use of Lucifer Yellow group alone, the combination with a Texas Red acceptor provides two to three fold increase in relative detection sensitivity in the 615 nm to 620 nm emission region.

Fluorescein fluorophores can be incorporated in the polynucleotide probe as a fluorescein isothiocyanate derivative obtainable from Molecular Probes, Inc., Junction City, Oreg., or Sigma Chemical Co., St. Louis, Mo. Texas Red sulfonyl chloride derivative of sulforhodamine 101 is obtainable from Molecular Probes, Inc. Texas Red can also be prepared from sulforhodamine 101 by reaction with phosphorous oxychloride, as described in Titus, et al., *J. Immunol. Meth.*, 50, pp. 193–204, 1982. Lucifer Yellow is obtainable from Aldrich Chemical Co., Milwaukee, Wis., as the vinyl sulfone derivative (Lucifer Yellow VS). Lucifer Yellow VS is a 4-amino-N-[3-vinylsulfonyl) phenyl]naphthalimide-3, 5-disulfonate fluorescent dye. For a description of its use, see Stewart, W., *Nature*, Vol. 292, pp. 17–21 (1981).

The foregoing description should not be understood as limiting the present invention to combinations of fluorescein with Texas Red or Lucifer Yellow with Texas Red. Those combinations preferred by the principles of the invention are more broadly applicable. The spacing feature of this invention can be utilized with other donor-acceptor pairs of fluorophores. For example, with fluorescein and Lucifer Yellow as donors, the acceptor fluorophore moieties prepared from the following fluorescent reagents are acceptable: Lissamine rhodamine B sulfonyl chloride; tetramethyl rhodamine isothiocyanate; rhodamine x isothiocyanate; and erythrosin isothiocyanate. Other suitable donors to the acceptors listed above (including Texas Red) are B-phycoerythrin and 9-acridineisothiocyanate derivatives.

When fluorescein is used as the acceptor moiety then suitable donors can be obtained from Lucifer Yellow VS; 9-acridineisothiocyanate; 4-acetamido-4'-isothiocyanatostilbene-2,2'-disulfonic acid; 7-diethylamino-3-(4'-isothiocyanatophenyl)-4-methylcoumarin.

When diethylenetriamine pentaacetate or other chelates of Lanthanide ions (Europium and Terbium) are used as acceptors, then suitable donors can be obtained from succinimdyl 1-pyrenebutyrate; and 4-acetamido-4'-isothiocyanatostilbene-2,2'-disulfonic acid derivatives.

Linker Arms

The length of the linker arms connecting the fluorescent moieties to the base units of the probes is also an important parameter for obtaining the full benefit of the present invention. The length of the linker arms for the purpose of the present invention is defined as the distance in Angstroms from the purine or pyrimidine base to which the inner end is connected to the fluorophore at its outer end. In general, the arm should have lengths of not less than 4 nor more than 30Å. The preferred length of the linker arms is from 10 to 25Å. The linker arms may be of the kind described in PCT application No. WO 84/03285. That application discloses a method for attaching the linker arms to the selected purine or pyrimidine base and also for attaching the fluorophore to the linker arm. The linker arm represented below is illustrative of the linker arms which may be employed for the purposes of the present invention as further described in the cited PCT application.

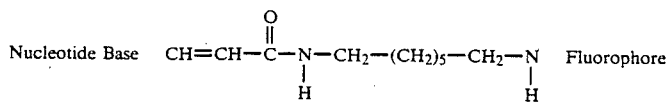

The linker arm as represented above contains 12 units in the chain and has a length of approximately 14Å. Use of this linker arm in preparing probes in accordance with the present invention is further illustrated in the experimental examples.

THE DRAWINGS

Figure 2:
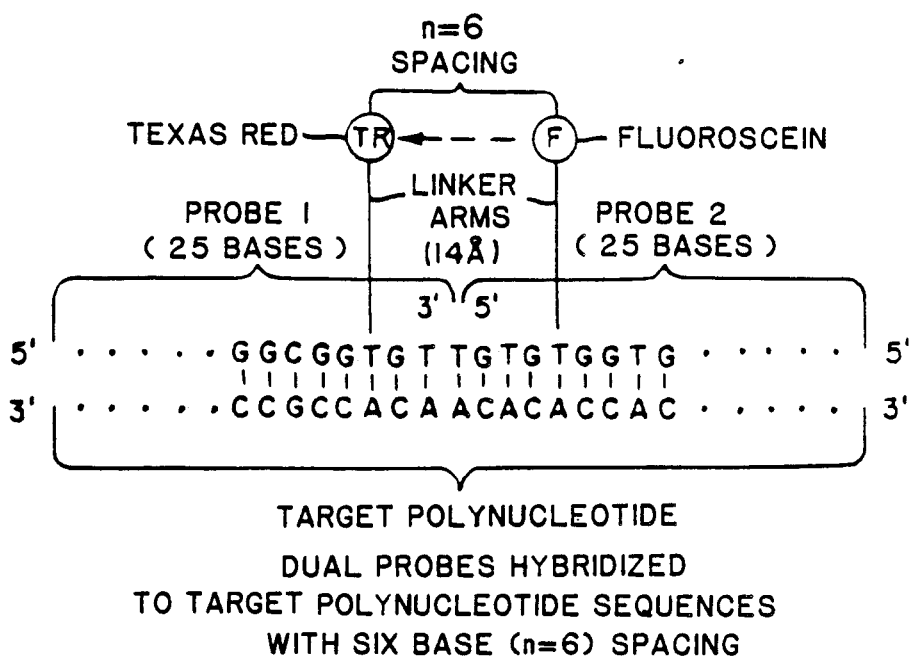

The drawing herein comprising FIGS. 1 and 2 provide diagrammatic illustrations of preferred embodiments. Referring first to FIG. 1, there is represented a single probe with 5 nucleotide base (n=5) spacing of the fluorophores. The polynucleotide probe may contain from 10 to 100 nucleotide bases. Intermediate the 5' and 3' ends of the probe, the donor fluorophore (D) and the acceptor fluorophore (A) are attached to base units through linker arms of 4 to 30Å. Units to which the linker arms connect the fluorophores are separated by 5 nucleotide based units (+5). The letters represent the bases of DNA: G for guanine, T for thymine, A for adenine, and C for cytosine. As indicated by the arrows, excitation light directed on the probe is absorbed by the donor fluorophore, transferred by the non-radiative energy process to the acceptor fluorophore, and emitted as fluorescent light by the acceptor fluorophore.

FIG. 2 illustrates dual probes hybridized to a target polynucleotide sequences of a nucleic acid sample. Both the sample and the probes contain the bases of DNA (G, T, A and C). In the hybridized condition, the nucleotide bases pair in the manner of double-stranded DNA (G-C and T-A). In the illustration given, each contains 25 nucleotide bases. Linker arms are attached to base units spaced from the adjacent 3', 5' ends of the probes as hybridized. Specifically, a Texas Red fluorophore is linked to a thymine unit (T) of probe 1, which is the third unit from the 3' end. Fluorescein is linked to a thymine (T) of probe 2, which is the fifth unit from the 5' end. When these dual probes are in hybridized relation, as shown, separation between the base units to which the donor and acceptor fluorophores are attached is 6 units (n=6). The linker arms have a length of approximately 14Å and may comprise the linker arm illustrated above.

Figure 3:
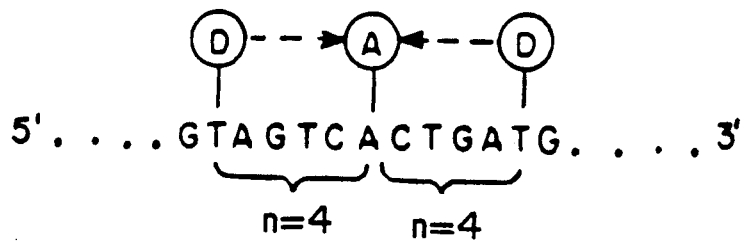
Figure 4:
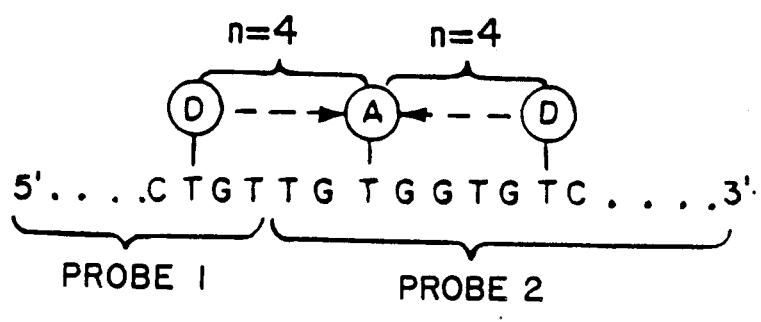

FIGS. 3 and 4 represent modifications of the probes in which single acceptor fluorophores arranged in space relation with a plurality of donor fluorophores. These embodiments employ the same spacing requirements discussed above with respect to the base unit separations and the linker arm lengths. FIG. 3 illustrates a single-probe embodiment in which an acceptor fluorophore is linked to an intermediate base positioned between two donor fluorophores linked to bases spaced from the base of the acceptor fluorophore by 4 base units (n=4). FIG. 4 illustrates a dual probe embodiment in which a donor fluorophore is linked to one probe and a donor and acceptor fluorophore to the other probe. As illustrated probe 1 has the donor fluorophore linked to the third base from its 3' end. Probe 2 has the acceptor fluorophore linked to the third base from its 5' end, and also has a donor fluorophore linked to the eighth base unit from the 5' end. This provides a spacing of four base units between the donor and acceptor fluorophores of probe 2 (n=4) when these probes are in hybridized relation to the target sequences as illustrated with respect to FIG. 2. Similar spacing (n=4) will be provided between the donor fluorophore of probe 1 and the acceptor fluorophore of probe 2. With the donor/acceptor fluorophore arrangements of FIGS. 3 and 4, the amount of nonradiative energy transferred to the acceptor fluorophore can be increased.

Figure 5:
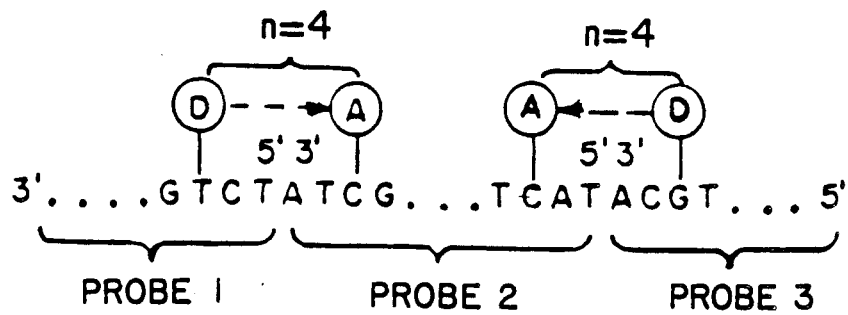

FIG. 5 shows a three probe embodiment which includes two pairs of donor and absorber fluorophores. Probe 1 has a donor moiety attached to the third base from its 5' end which as hybridized to the target polynucleotide pairs with the absorber moiety on probe 2 which is attached to the third base from its 3' end, giving a separation of 4 base units (n=4). The 5' end of probe 2 has an acceptor moiety attached to the third base which when hybridized pairs with a donor moiety on probe 3 attached to the third base to also provide an n=4 spacing.

Assay Procedures

The probes of this invention may be employed in either heterogeneous or homogeneous assays of the kind heretofore used for DNA or RNA hybridization assays. To obtain the maximum benefit of the invention, however, it is preferred to employ the probes in conjunction with heterogeneous assays in which the target DNA or RNA is hybridized to a support. The test samples containing the target sequences may be prepared by any one of a number of known procedures and attached to suitable immobilization support matrices. Such procedures are described in *Methods in Enzymology*, Vol. 66, pp. 379–469 (1979), Vol. 65, Part 1, pp. 468–478 (1980, and *Analytical Biochemistry*. 138, pp. 267–284 (1984). See also U.S. Pat. No. 4,358,539 and published European Patent Applications Nos. 0 070 685 and 0 070 687. The usual supports used in hybridization assays include nitrocellulose filters, nylon (Zetabind) filters, polystyrene beads, and Agarose beads to name a few. Further details of a typical heterogeneous assay procedure are set out in one of the following examples. The probes of this invention, their method of use, and the results obtained are further illustrated by the following examples.

EXAMPLE I

By way of specific illustration, the preparation of a polynucleotide probe containing a fluorescein and a Texas Red moiety with an n=5 spacing can be carried out as follows. The starting material is approximately 300μg of the appropriate synthetic (25mer) polynucleotide probe containing two primary amine functionalized linker arm nucleotides separated by five nucleotides within the sequence. The 300μg of polynucleotide is taken up in about 20μl of 0.5M sodium bicarbonate buffer at pH 8.8. About 100μg of Texas Red dissolved in 10μl of water is added to the polynucleotide solution. A limited reaction is carried out at 0°–5° C. for approximately 15 minutes. At this point about 10μl of a 7M urea solution is added and the reaction mixture is separated over a 0.7cm×3.0cm G-25 Sephadex Column. The initial fractions (excluded volume) contain the unreacted polynucleotide, mono-substituted Texas Red polynucleotide probe, and di-substituted Texas Red polynucleotide probe. The final fractions (included volume) contain the unreacted Texas Red. The inital fractions are pooled and lyophilized, and the final fractions are discarded. The lyophilized pooled fractions are brought up in a small volume (5-10μl) of 3.5M urea for separation by gel electrophoresis.

Electrophoresis on a 20% polyacrylamide gel (7-8M urea) separates the sample into three distinct bands, the lower is the unreacted polynucleotide, the middle band is the mono-substituted Texas Red polynucleotide, and the upper band is the di-substituted Texas Red polynucleotide. Reaction conditions were originally controlled in order to prevent total conversion of the polynucleotide to the di-substituted Texas Red polynucleotide derivative. At this point the band containing the mono-substituted Texas Red polynucleotide derivative is carefully excised from the gel and the derivative is extracted with water, and the resulting solution lyophilized to dryness. The lyophilized sample is now taken up in a small volume of water and desalted on a G-25 Sephadex column. The fractions containing the mono-substituted Texas Red polynucleotide probe are pooled and lyophilized.

The sample is now ready for the second reaction to incorporate the fluorescein moiety into mono-substituted Texas Red polynucleotide probe. The sample is again taken up in about 20μl of 0.5M sodium bicarbonate buffer at pH 8.8. About 500μg of fluorescein isthiocyanate (FITC) in 10μl water is added to the buffered solution containing the mono-substituted Texas Red polynucleotide probe. The reaction is carried out at 0°-5° C. for about two hours. About 10μl of a 7M urea solution is added, and the sample is run over another G-25 Sephadex column, as described previously, to separate reacted polynucleotide probe from FITC. Again appropriate fractions are pooled and lyophilized. The sample is again electrophoresed on a 20% polyacrylamide gel, separating the sample into two bands: the lower being unreacted monosubstituted Texas Red polynucleotide probe and the upper band being the fluorescein and Texas Red substituted polynucleotide probe. The upper band is carefully excised, extracted, lyophilized, and desalted on a G-25 Sephadex column as was described above. The final purified fluorescein-Texas Red polynucleotide probe is then analyzed by UV/Visible spectroscopy. The ratio of adsorption (O.D.) at 260 nm, 492 nm, and 592 nm can be used to determine proper stoichiometry for the probe; the 25mer polynucleotide probe contains one fluorescein and one Texas Red moiety.

The synthesis and purification of probes containing a single fluorophore is straightforward. The starting material is a 25mer polynucleotide probe containing only one amine functionalized linker arm nucleotide incorporated at the appropriate position within the probe. In the case of both Texas Red and FITC, the reactions are carried out for a longer time (about two hours) in order to increase yield of the fluorophore substituted probe. Subsequent steps for purification are the same as those described above.

EXAMPLE II

A series of fluorescein-Texas Red 25mer polynucleotide probes (F&TR probes) were prepared in which the separation between the fluorophore moieties was n=0, n=1, n=5, n=6, n=9, and n=12. The probes were designed to hybridize to Herpes Simplex Virus (type 1) target DNA. The procedure was as described in Example I using the 14Å linker arm previously illustrated. The actual sequence and relative position of fluorophores in the n=5, F&TR probe is shown below.

5'-TGTGTGGTGTAGATGTTCGCGATTG-3'

It should be pointed out that the fluorophores can occupy either linker arm position on the probe. But each probe contains only one fluorescein and one Texas Red. Fluorescent analysis was carried out on samples containing from 200ng to 2μg of the F&TR probe in 250μl of 0.01M sodium phosphate (pH7.6), 0.1M sodium chloride buffer.

Fluorescent emission spectra were obtained for samples at 490 nm, the approximate excitation maximum for the donor (fluorescein) and at 590 nm, the approximate excitation maximum for the acceptor (Texas Red). All values were corroborated by also obtaining the fluorescent excitation spectra for each of the F&TR probes in the series. Observed energy transfer efficiency, in terms of fluorescent emission of the acceptor, was determined by taking the ratio for fluorescent emission at 615 nm for the F&TR probe excited at 490 nm (excitation of donor, fluorescein) to the fluorescent emission at 615 nm for a single labelled Texas Red probe (TR probe) excited at 590 nm (excitation for the acceptor, Texas Red) multiplied by 100.

Observed Energy Transfer Efficiency =

$$\frac{(F\&TR \text{ Probe } Em \text{ 615 nm at } EX \text{ 490 nm})}{(TR \text{ Probe } EM \text{ 615 nm at } EX \text{ 590 nm})} \times 100$$

Thus, a value of "75" means that the F&TR probe when excited at 490 nm produces 75% of the fluorescent emission (615 nm) of an equal amount (in terms of Texas Red) of a TR probe excited at 590 nm. Observed energy transfer efficiencies were determined for the complete F&TR probe series both hybridized to a complementary target polynucleotide and unhybridized. Results for the F&TR probe series is given in Table A.

TABLE A

Observed Energy Transfer Efficiencies for Fluorescein-Texas Red Probes

| F&TR Probe (N) | (Emission 615 nm, Excitation 490 nm) | |
|---|---|---|
| | Unhybridized | Hybridized |
| 0 | 25 | 17 |
| 1 | 29 | 31 |
| 5 | 35 | 82 |
| 6 | 39 | 59 |
| 9 | 50 | 30 |
| 12 | 17 | 13 |
| TR Probe (EX 590 nm) | 100 | 100 |

The results in Table A show that the observed energy transfer efficiency is highest (82) for the n=5 F&TR probe in the hybridized series. In the hybridized series, energy transfer is observed to decrease for the probes with the longer donor-acceptor distances (n=6, 9, 12) as would be expected from the Förster equation. However, unexpectedly the efficiencies also drop off for the n=0 and n=1 probes, with the closer donor-acceptor distances.

The F&TR probe series does not follow the expected type of behavior. The high energy transfer efficiency is only found for a relatively restricted number of positions approximated to be between 20 to 30Å. These high efficiency positions are believed to include the n=3 and n=4 positions as well as the experimentally determined n=5 and n=6, and also the n=7 position.

Table A also shows that the results for the unhybridized F&TR probe series are similar to the hybridized series, but less pronounced. Again, the n=0 and n=1 values are lower than would be expected from the Förster equation. The highest observed efficiency value is 50, and this is for the n=9 F&TR probe. It appears that hybridization provides an improved environment which leads to a higher overall observed energy transfer efficiency at or near the n=5 position, as well as causing a lowering of efficiency at the n=0 and n=1 positions.

EXAMPLE III

Two sets of dual 25mer probes were prepared using the same procedure and linker arms as in Example III. The final separation of fluorescein and Texas Red (upon hybridization to target polynucleotide) was n=0 and n=6 base pair units.

Results for the fluorescent analysis of Probe Set 1 (n=0) and Probe Set 2 (n=6) hybridized to complementary target polynucleotide are given in Table B:

TABLE B

| Observed Energy Transfer Efficiencies for Dual Probes (Fluorescein Probe and Texas Red Probe) Hybridized to Target Polynucleotide | | |
|---|---|---|
| Probe Set | Base Pair Separation (n) | (Emission 615 nm, Excitation 490 nm) |
| 1 | 0 | 15 |
| 2 | 6 | 52 |

The results in Table B show that the observed energy transfer efficiency is highest for Probe Set 2 (n=6) and unexpectedly lower for Probe Set 1 (n=0). The results for the dual probe system corroborate the results obtained for the single F&TR probe series. Again, the dual probe results indicate that there is a unique narrow range of optimal positions around the n=6 base pair spacing.

EXAMPLE IV

A 25mer probe containing Lucifer Yellow as the donor and Texas Red as the acceptor (LY&TR probe) with an n=5 nucleotide spacing was prepared using the basic procedures described earlier. Observed energy transfer efficiency, in terms of emission at 615 nm when excited at 435 nm, was found to be approximately 20%. The relative value is lower than the value of 82% for the n=5 F&TR probe. The lower "relative" value is due to the fact that the extinction coefficient of Lucifer Yellow is significantly lower than fluorescein, ~12,000 for Lucifer Yellow versus 75,000. for fluorescein. Lucifer Yellow because of this property is not as "good" a donor as fluorescein. However, the Lucifer Yellow/Texas Red pair produces a large Stokes shift (~170 nm) and the donor can be excited by a laser (Helium-Cadmium, ~442 nm).

EXAMPLE V

The example detailed here concerns the use of single probes of Example II used in a sandwich type heterogeneous assay format to detect Herpes Simplex Virus DNA. By way of background the sandwich type assay involves the initial capture, via hybridization, of the given target polynucleotide by a complementary probe (capture probe) immobilized on some type of support material (polystyrene or Agarose beads). The now captured (immobilized by hybridization) target polynucleotide is contacted with another complementary probe which has been labelled with a reporter group (fluorophore, etc.). The now hybridized reporter probe signals the presence of the target polynucleotide sequence.

In the assay procedure about 50 to 100 Agarose Herpes Simplex Virus (HSV) capture beads (~100 micron diameter) are employed. The Agarose HSV capture beads were prepared by substitution (covalent linkage) of appropriate complementary HSV probes (20-50 nucleotides in chain length) to an activated form of Agarose beads. Sample DNA (~1-10 mg) containing Herpes Simplex Virus DNA is prepared in a final volume of ~100μl of hybridization buffer (0.75M sodium chloride, 0.075M sodium citrate, 1% (w/v) sodium dodecyl sulfate (SDS), 500μg bovine serum albumin, (Crystalline Pentex Fraction V), 500μg polyvinylpyrollidone).

The Agarose HSV capture beads are added to the DNA sample solution. The sample solution is gently agitated and hybridization is carried out at 45°-55° C. for 15-30 minutes. The beads are now separated from the sample solution by filtration or centrifugation. The Agarose HSV capture beads are now washed three times with 2ml volumes of 1×SSC+0.1% SDS buffer (0.15M sodium chloride, 0.015M sodium citrate, 0.1% (w/v) SDS, pH7.15, 45°-50° C.). The Agarose HSV capture beads are now suspended in another 100μl of hybridization buffer containing 10-100 ng of the fluorescein-Texas Red HSV 25mer probe (Example II). Hybridization is again carried out at 45°-55° C. for 15-30 minutes with gentle agitation. The beads are again separated from the solution by filtration or centrifugation. The beads are first washed three times with 2ml volumes of 1×SSC+0.1% SDS buffer at 45°-55° C.; then three times with 1×SSC buffer. The beads are now transferred to a microscope slide or appropriate sample cell for fluorescent analysis. Fluorescent analysis is carried out with a photon counting epifluorescent microscope system. Excitation is carried out with either an argon ion laser; a high intensity mercury (Hg) arc lamp; or other high intensity light source appropriately filtered for excitation in the 480-490 nm region. The epifluorescent microscope contains the appropriate dichroic mirror and filters for monitoring fluorescent emission in the 615-630 nm region. Fluorescent emission is quantitated using a photon counting photomultiplier system coupled to the microscope. Individual Agarose beads containing target DNA to which fluorescent probe has hybridized are counted for 1-10 seconds. Usually about 10-15 beads per sample are counted. Total time for fluorescent analysis of a sample is less than five minutes.

A second method for fluorescent analysis of the Agarose bead samples involves side illmination of the beads with a fiber optic light source. In this procedure excitation light does not enter the microscope, but is focused into a 50 to 100 micron fiber optic which is positioned in the sample cell (slide) for side illumination of the beads. The excitation light now being external and at a 90° angle to the microscope objective.

We claim:

1. The spectroscopy method for detecting a target single-strand polynucleotide sequence in a polynucleotide sample in which either (i) a fluorescent polynucleotide single probe sequence complementary to said target sequence is hybridized thereto, or (ii) a plurality of probes of such sequences complementary to sequentially adjacent portions of said target sequences are hybridized thereto, wherein the improvement comprises having present in said single probe or in said plurality of probes at least one pair of fluorescent moieties connected by linker arms to nucleic acid base units, said fluorescent moieties comprising respectively donor and acceptor moieties selected so that the emission spectrum of the donor moiety overlaps the excitation spectrum of the acceptor moiety to permit non-radioactive energy transfer with efficient fluorescent emission by the acceptor fluorophores, the wavelength maximum of the emission spectrum of the acceptor moiety being at least 100 nm greater than the wavelength maximum of the excitation spectrum of the donor moiety, said linker arms having lengths of 4 to 30 Angstroms, the donor and acceptor moieties being connected to non-contiguous base units in said single probe or to base units in said plural probes other than 3' and 5' and units thereof, when said single probe or said plural probes are hybridized to the target sample the base units to which said donor and acceptor moieties are connected being paired through hybridization to base units of said target sequence which are separated by 2 to 7 intervening nucleotide base units of the target sequence.

2. The method improvement of claim 1 in which said donor and acceptor moieties are on a single probe.

3. The method improvement of claim 1 in which said donor and acceptor moieties are on a pair of probes.

4. The method of claim 1, 2, or 3 in which said donor moiety is fluorescein and said acceptor moiety is Texas Red.

5. The method of claim 1 in which said linker arms have lengths of from 10 to 25 Angstroms.

6. The method of claim 1 in which when said single probes or said dual probe are hybridized to the target sequence the base units connected to said donor and acceptor moieties are paired with nucleotide base units of the target sequence which are separated by 3 to 6 intervening base units.

7. The spectroscopy method for detecting a target single-strand polynucleotide sequence in a polynucleotide sample immobilized on a support in which either (i) a fluorescent polynucleotide single probe sequence complementary to said target sequence is hybridized thereto, or (ii) a plurality of probes of such sequences complementary to sequentially adjacent portions of said target sequences are hybridized thereto, said probes being synthetic polynucleotides of from 10 to 100 base units in length, wherein the improvement comprises having present in said single probe or in said plurality of probes at least one pair of fluorescent moieties connected by linker arms to nucleic acid base units, said fluorescent moieties comprising respectively donor and acceptor moieties selected so that the emission spectrum of the donor moiety overlaps the excitation spectrum of the acceptor moiety to permit non-radiative energy transfer with efficient fluorescent emission by the acceptor fluorophore, the wavelength maximum of the emission spectrum of the acceptor moiety being at least 100 nm greater than the wavelength maximum of the excitation spectrum of the donor moiety, said linker arms having lengths of 10 to 25 Angstroms, the donor and acceptor moieties being connected to non-contiguous base units in said single probe and to base units in said plural probes other than the 3' and 5' end units, when said single probe or plural probes are hybridized to the target polynucleotide the base units to which said donor and acceptor moieties are connected being paired with hybridized base units of said target sequence which are separated by 2 to 7 intervening nucleotide base units of the target sequence.

8. The method of claim 7 in which said donor and acceptor moieties are on a single probe.

9. The method of claim 7 in which said donor and acceptor moieties are on a pair of probes.

10. The method of claim 7, 8, or 9 in which said donor moiety is fluorescein and said acceptor moiety is Texas Red.

11. The method of claim 1 or 7 in which said donor and acceptor moieties are on a single probe and are connected to base units thereof other than the 3' and 5' end units and which are separated by 4 to 6 intervening base units.

12. The method of claim 1 or 7 in which said moieties are on a pair of probes respectively having 3' and 5' ends hybridizing to adjacent base units of the target polynucleotide and when so hybridized the donor and acceptor moieties being separated by 4 to 6 intervening base units.

13. The methods of claim 11 or 12 in which said donor moiety is fluorescein and said acceptor moiety is Texas Red.

14. A polynucleotide probe for fluorescent spectroscopy assaying of a target single-stranded polynucleotide, comprising a synthetic single-stranded polynucleotide containing from 10 to 100 nucleic acid base units, two of said base units having respectively attached thereto by separate linker arms a donor fluorescent moiety and an acceptor fluorescent moiety, said fluorescent moieties being selected so that the emission spectrum of the donor moiety overlaps the excitation spectrum of the acceptor moiety to permit non-radiative energy transfer with efficient fluroescent emission by the acceptor fluorophore, the wavelength maximum of the emission spectrum of the acceptor moiety being at least 100 nm greater than the wavelength maximum of the excitation spectrum of the donor moiety, said linker arms having lengths of 4 to 30 Angstroms, said donor and acceptor moieties being connected to base units other than the 3' and 5' end units and which units are separated by 2 to 7 intervening base units.

15. The probe of claim 14 in which said linker arms have lengths of from 10 to 25 Angstroms.

16. The probe of claim 14 in which said donor moiety is fluorescein and said acceptor moiety in Texas Red.

17. A polynucleotide probe for fluorescent spectroscopy assaying of a target single-stranded polynucleotide, comprising a synthetic single-stranded polynucleotide containing from 10 to 100 nucleic acid base units, two of said base units having respectively attached thereto by linker side chains a donor fluorescent moiety and an acceptor fluorescent moiety, said fluorescent moieties being selected so that the emission spectrum of the donor moiety overlaps the excitation spectrum of the acceptor moiety to permit non-radiative energy transfer with efficient fluorescent emission by the acceptor fluorophore, the wavelength maximum of the emission spectrum of the acceptor moiety being at least 100 nm greater than the wavelength maximum of the excitation spectrum of the donor moiety, said linker side chains having lengths of 10 to 25 Angstroms, said donor and acceptor moieties being connected to base units other than the 3' and 5' end units and which units are separated by 3 to 6 intervening base units.

18. The probe of claim 17 in which said donor moiety is fluorescein and said acceptor moiety is Texas Red.

19. A pair of polynucleotide probes for fluorescent spectroscopy assaying of a target single-stranded polynucleotide, comprising first and second synthetic single-stranded polynucleotide probes each containing from 10 to 100 nucleic acid base units, said probes hybridizing to adjacent sequences of said target polynucleotide with the 3' end of the first probe adjacent to the 5' end of the second probe, said probes having fluorescent moieties attached to base units thereof other than said adjacent 3' and 5' end units by linker arms having lengths of 4 to 30 Angstroms, one of said arms being connected to a donor moiety and other to an acceptor moiety, said moieties being selected so that the emission spectrum of the donor moiety overlaps the excitation spectrum of the acceptor moiety to permit non-radiative energy transfer with efficient fluorescent emission by the acceptor fluorophore, the wavelength maximum of the emission spectrum of the acceptor moiety being at least 100 nm greater than the wavelength maximum of the excitation spectra of the donor moiety, said linker arms having lengths of from 4 to 30 Angstroms, and being connected to base units other than the 3' and 5' end units, when said probes are hybridized to the target polynucleotide sequences the base units to which said donor and acceptor moieties are connected being paired with hybridized base units of said target sequences which are separated by 2 to 7 intervening base units.

20. The pair of probes of claim 19 in which said linker arms have lengths of from 10 to 25 Angstroms.

21. The pair of probes of claim 19 in which said donor moiety is fluorescein and acceptor moiety is Texas Red.

22. A pair of polynucleotide probes for fluorescent spectroscopy assaying of a target single-stranded polynucleotide, comprising first and second synthetic single-stranded polynucleotide probes hybridizing to adjacent sequences of said target polynucleotide with the 3' end of the first probes adjacent to the 5' end of the second probe, said probes having fluorescent moieties attached to base units other than said adjacent 3' and 5' end units by linker arms having lengths of 10 to 25 Angstroms, one of said side chains being connected to a donor moiety and the other to an acceptor moiety, said moieties being selected so that the emission spectrum of the donor moiety overlaps the excitation spectrum of the acceptor moiety to permit non-radiative energy transfer with efficient fluorescent emission by the acceptor fluorophore, the wavelength maximum of the emission spectrum of the acceptor moiety being at least 100 nm greater than the wavelength maximum of the excitation spectrum of the donor moiety, said linker arms having lengths of from 10 to 25 Angstroms, and being connected to base units other than the 3' and 5' end units when said probes are hybridized to the target polynucleotide sequences the base units to which said donor and acceptor moieties are connected being paired with base units of the target sequences which are separated by 4 to 6 intervening base units.

23. The pair of probes of claim 22 in which said donor moiety is fluorescein and said acceptor moiety is Texas Red.

24. A method of detecting a target nucleic acid comprising hybridizing a poly- or oligonucleotide probe or proves to said nucleic acid, wherein said probe or probes have or hybridize to form a pair of fluorescent moieties connected to separate nucleotides and wherein the nucleotides connected to the fluorescent moieties are separated by as least two but not more than seven nucleotides, and detecting the hybridization by fluorescent means based on the interaction between the moieties.

25. The method of claim 24, wherein the fluorescent moieties are separated by at least three but not more than six nucleotides.

26. The method of claim 24, wherein the fluoescent moieties are separated by at least four but not more than six nucleotides.

27. A poly- or oligonucleotide probe comprising a pair of fluorescent moieties connected to separate nucleotides and wherein the nucleotides connected to the fluorescent moieties are separated by at least two but not more than seven nucleotides.

28. The nucleotide probe of claim 27, wherein the fluorescent moieties are separated by at least three but not more than six nucleotides.

29. The nucleotide probe of claim 27, wherein the fluorescent moieties are separated by at least four but not more than six nucleotides.

* * * * *

UNITED STATES PATENT AND TRADEMARK OFFICE
CERTIFICATE OF CORRECTION

PATENT NO. : 4,996,143

DATED : February 26, 1991

INVENTOR(S) : Michael J. Heller and Edward G. Jablonski

It is certified that error appears in the above-identified patent and that said Letters Patent is hereby corrected as shown below:

On the title page:

In [75], delete "Edward J. Jablonski" and insert therefor --Edward G. Jablonski--.

In column 9, line 30, delete "isthiocyanate" and insert therefor --isothiocyanate--.

In column 13, line 15, delete "non-radioactive" and insert therefor --non-radiative--.

In column 14, line 14, delete "of" and insert therefor --or--.

In column 16, line 22, delete "proves" and insert therefor --probes--.

In column 16, line 26, delete "as" and insert therefor --at--.

Signed and Sealed this

Fifth Day of January, 1993

*Attest:*

DOUGLAS B. COMER

*Attesting Officer*  *Acting Commissioner of Patents and Trademarks*